United States Patent
Tomasetti et al.

(12)

(10) Patent No.: US 6,234,672 B1
(45) Date of Patent: May 22, 2001

(54) MINIATURE C-ARM APPARATUS WITH C-ARM MOUNTED CONTROLS

(75) Inventors: Perry J. Tomasetti, Elmwood Park; Sandra L. Brown, Belvidere; Scott M. Keane, Mount Prospect, all of IL (US)

(73) Assignee: FluoroScan Imaging Systems, Inc., Northbrook, IL (US)

( * ) Notice: Subject to any disclaimer, the term of this patent is extended or adjusted under 35 U.S.C. 154(b) by 0 days.

(21) Appl. No.: 09/270,373

(22) Filed: Mar. 16, 1999

Related U.S. Application Data

(60) Provisional application No. 60/078,491, filed on Mar. 18, 1998.

(51) Int. Cl.⁷ .................................................. H05G 1/02
(52) U.S. Cl. ........................... 378/197; 378/198; 378/114
(58) Field of Search ................................... 378/197, 198, 378/114, 116

(56) References Cited

U.S. PATENT DOCUMENTS 5,917,883 * 6/1999 Khutoryansky et al. ............. 378/116
6,007,243 * 12/1999 Ergun et al. .......................... 378/197

* cited by examiner

Primary Examiner—Robert H. Kim
Assistant Examiner—Pamela R. Hobden
(74) Attorney, Agent, or Firm—Cooper & Dunham LLP

(57) ABSTRACT

Mini C-arm apparatus for x-ray fluoroscopic imaging having a base or cabinet, an articulated arm assembly connected thereto, a support arm assembly carried by the articulated arm assembly, a C-arm slidably mounted in the support arm assembly, and an x-ray source assembly including an x-ray source and an image receptor assembly including an image receptor respectively mounted at opposed locations on the C-arm such that x-rays emitted by the x-ray source impinge on the image receptor, wherein one of the source and image receptor assemblies includes a control panel that permits activation of predefined functions of the x-ray fluoroscopic imaging apparatus.

8 Claims, 9 Drawing Sheets

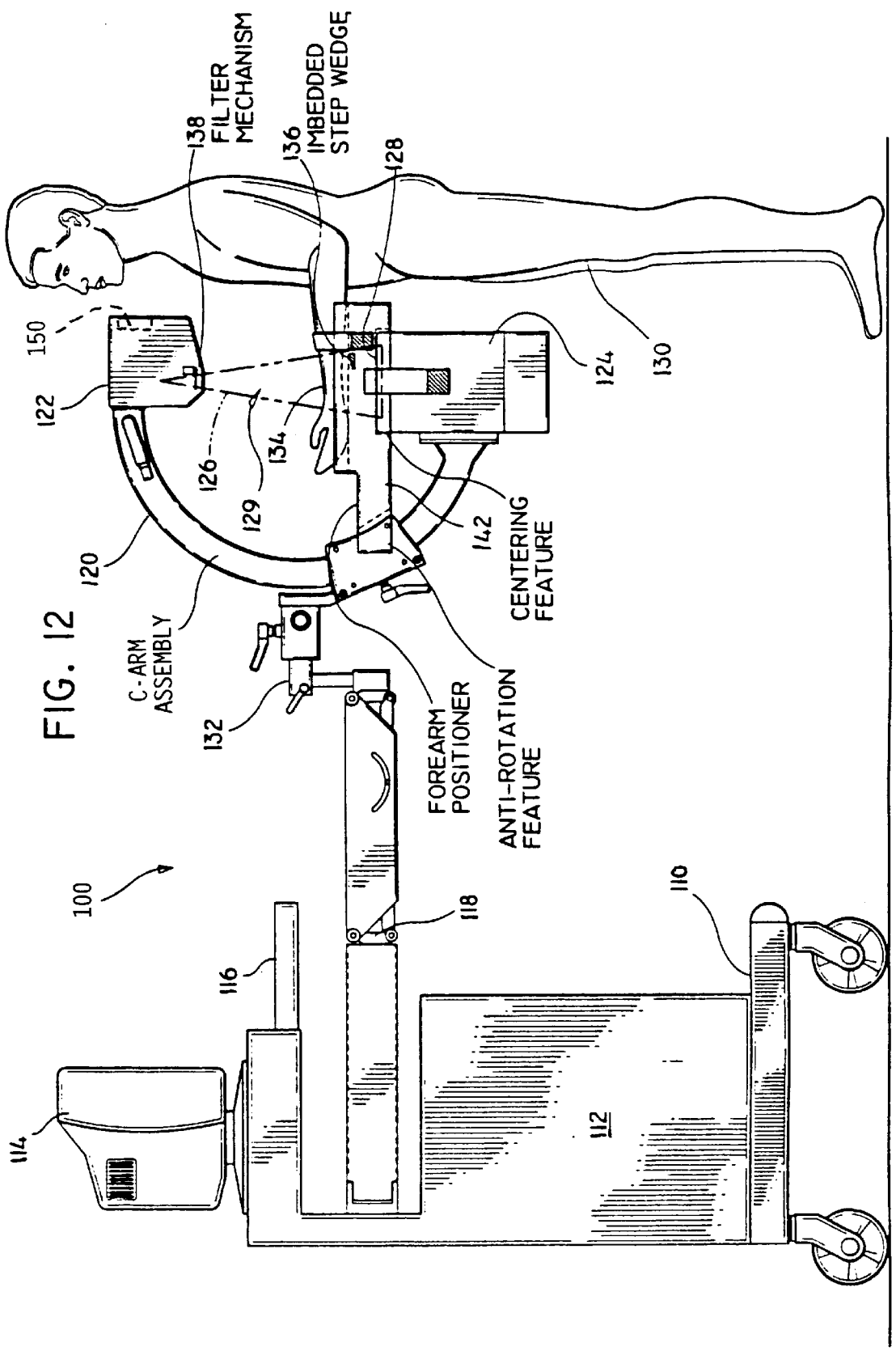

MINIATURE C-ARM APPARATUS WITH C-ARM MOUNTED CONTROLS

CROSS REFERENCE TO RELATED APPLICATION

This application claims the priority benefit, under 35 U.S.C. §119(e)(1), of applicants' U.S. provisional application Ser. No. 60/078,491, filed Mar. 18, 1998, which is incorporated herein in its entirety by this reference.

BACKGROUND OF THE INVENTION

This invention relates to mobile x-ray fluoroscopic imaging systems with miniature C-arm apparatus, and more particularly to miniature C-arm apparatus having C-arm mounted controls which activate certain functions of the imaging system.

In present-day medical practice, x-ray fluoroscopic imaging systems provide images of bone and tissue that are similar to conventional film x-ray shadowgrams but are produced by conversation of an incident x-ray pattern to a "live" enhanced (intensified) optical image that can be displayed on a video monitor directly, i.e., essentially contemporaneously with the irradiation of the patient's body or body portion being imaged. The term "fluoroscopic imaging" is used herein to designate such provision of directly video-displayed x-ray images. An imaging device, including an image intensifier, suitable for use in such a system is described in U.S. Pat. No. 4,142,101, which is incorporated herein in its entirety by this reference.

In some x-ray fluoroscopic imaging systems, the entire system is carried on an easily movable cart and an x-ray source and detector are mounted on a rotatable mini C-arm dimensioned for examining smaller body parts such as the extremities (wrists, ankles, etc.) of a human patient.

One illustrative example of a commercially available mini C-arm x-ray fluoroscopic imaging system is that sold under the trade name "FluoroScan III" by FluoroScan Imaging Systems, Inc., of Northbrook, Ill. Further examples of mini C-arm x-ray fluoroscopic imaging systems are described in U.S. Pat. No. 5,627,873 and copending U.S. patent application Ser. No. 09/199,952, filed Nov. 24, 1998 (and assigned to the same assignee as the present application), both of which are incorporated herein in their entirety by this reference.

Mini C-arm x-ray fluoroscopic imaging systems are also being used to measure bone mineral density (BMD) of bones in, for example, the forearm or wrist, or in the ankle or heel (calcaneal region) of a human patient. An example of such an x-ray fluoroscopic imaging system is described in allowed copending U.S. patent application Ser. No. 08/794, 615 filed on Feb. 3, 1997 which is assigned to Hologic, Inc., the parent company of the assignee of the present application, and which is incorporated herein in its entirety by this reference.

Generally, such mini C-arm x-ray fluoroscopic imaging systems and x-ray bone densitometry systems are economical in space, conveniently movable (as within a hospital, clinic or physician's office) to a desired temporary location of use, and offer superior safety (owing to low levels of electric current utilization and reduced exposure of personnel to scatter radiation) as well as ease of positioning the x-ray source and detector relative to a patient's extremity for imaging. The various functions and operations of the system are conventionally controlled by buttons or switches on a control panel that is positionally associated with the cart.

SUMMARY OF THE INVENTION

The x-ray fluoroscopic imaging system according to the present application includes a processing system, such as a computer, and peripheral devices enclosed within a portable cabinet and a C-arm apparatus that is mounted to the cabinet. The processing system controls the operation of the various components of the imaging system, provides a camera or image processing to transform in real time image data received from an image receptor for display, printing or storage, and communicates with peripheral devices. The computer may also be configured to communicate with a local area network to transfer, for example, image data to locations remote from the sterile environment. An example of a suitable processing system is a personal computer running the "Windows 95"®, DOS, UNIX, MacOS or other operating systems. Examples of peripheral devices include display monitors, image (or video) printers and image storage devices (or recorders).

The C-arm apparatus includes a C-arm assembly, a support arm assembly and an articulating arm assembly. The C-arm assembly includes a C-arm having a track for guiding rotational movement of the C-arm, an x-ray source assembly including an x-ray source and an x-ray detector assembly including an image receptor and camera. The x-ray source and detector assemblies are located at opposing ends of the C-arm so that the x-ray source and image receptor face each other and x-rays emitted by the x-ray source impinge on the image receptor.

The support arm assembly engages the C-arm track so that the C-arm is movable relative to the support arm, and the articulating arm assembly is provided to facilitate movement of, including change in the angular orientation of, the source and detector assemblies relative to a patient's body portion being imaged. The articulating arm assembly includes at least one movable arm (which may be, e.g., a single member, or an articulated element constituted of two or more pivotally interconnected members) wherein a first end portion of the arm is connected to the support arm assembly and a second end portion of the arm is connected to a mobile base or portable cabinet. Preferably, the first end portion is so connected to the support arm assembly that the support arm assembly can be rotated relative to the movable arm.

During surgical procedures a sterile field is created around a patient to ensure that foreign substances or organisms do not infect the patient. Any instruments or persons within this field have to be sterile or covered by a sterile draping material. The sterile field is generally defined by the American College of Surgeons and published by the Association of Operating Room Nurses (AORN). Generally, the sterile field is defined as the area occupied by the sterile draping material on any operating room table, including the patient table and instrument tables. To permit sterile personal to position the x-ray fluoroscopic imaging system C-arm assembly in the sterile field a clear surgical drape covers the C-arm assembly.

In accordance with the present invention, and as a particular feature thereof, to permit surgeons to activate certain functions of the x-ray fluoroscopic imaging system within this sterile field, at least one of the x-ray source assembly or the x-ray detector assembly, both of which are used within the sterile field, includes a control panel that provides a physician with easy access to predefined imaging control functions associated with the x-ray fluoroscopic imaging system within the sterile field. The control panel may include audio and/or visual indicators to alert the physician and others to the activation of certain functions of the system, such as the x-ray source. By thus locating the control panel on an end of the C-arm, a surgeon can activate the functions without placing a hand or arm in the path of the x-ray beam.

In a preferred embodiment, this control panel includes an array of membrane switches, wherein each switch in the array is provided to activate a function performed by the x-ray fluoroscopic imaging system. Examples of functions controlled by the control panel switches include: x-ray source activation; image printing; image noise suppression; camera rotation; and x-ray source voltage/current control. However, it is also contemplated that other functions or all of the functions of the x-ray fluoroscopic imaging system can be controlled by the control panel on an end of the C-arm. For ease of use each membrane switch in the array has a raised button profile which provides tactile feedback, completes a signal circuit when contact material mounted on the underside of the raised button profile is depressed against a base layer, and breaks the signal circuit when pressure on the contact material is released. The raised button profile of each switch provides a tactile response so that a surgeon wearing protective surgical gloves can feel when a switch is being depressed and released.

The x-ray fluoroscopic imaging system may also include a foot control panel which is similar to the above-described control panel but permits foot activation of predefined functions of the x-ray fluoroscopic imaging system including but not limited to x-ray activation, image printing and image storing.

Further features and advantages of the invention will be apparent from the detailed description hereinbelow set forth, together with the accompanying drawings.

BRIEF DESCRIPTION OF THE DRAWINGS

FIG. 12 is a simplified and partly schematic side elevational view of a mini C-arm x-ray fluoroscopic imaging system arranged for use to measure forearm BMD of a human patient, in which an embodiment of the present invention may be incorporated.

DETAILED DESCRIPTION

Figure 1:
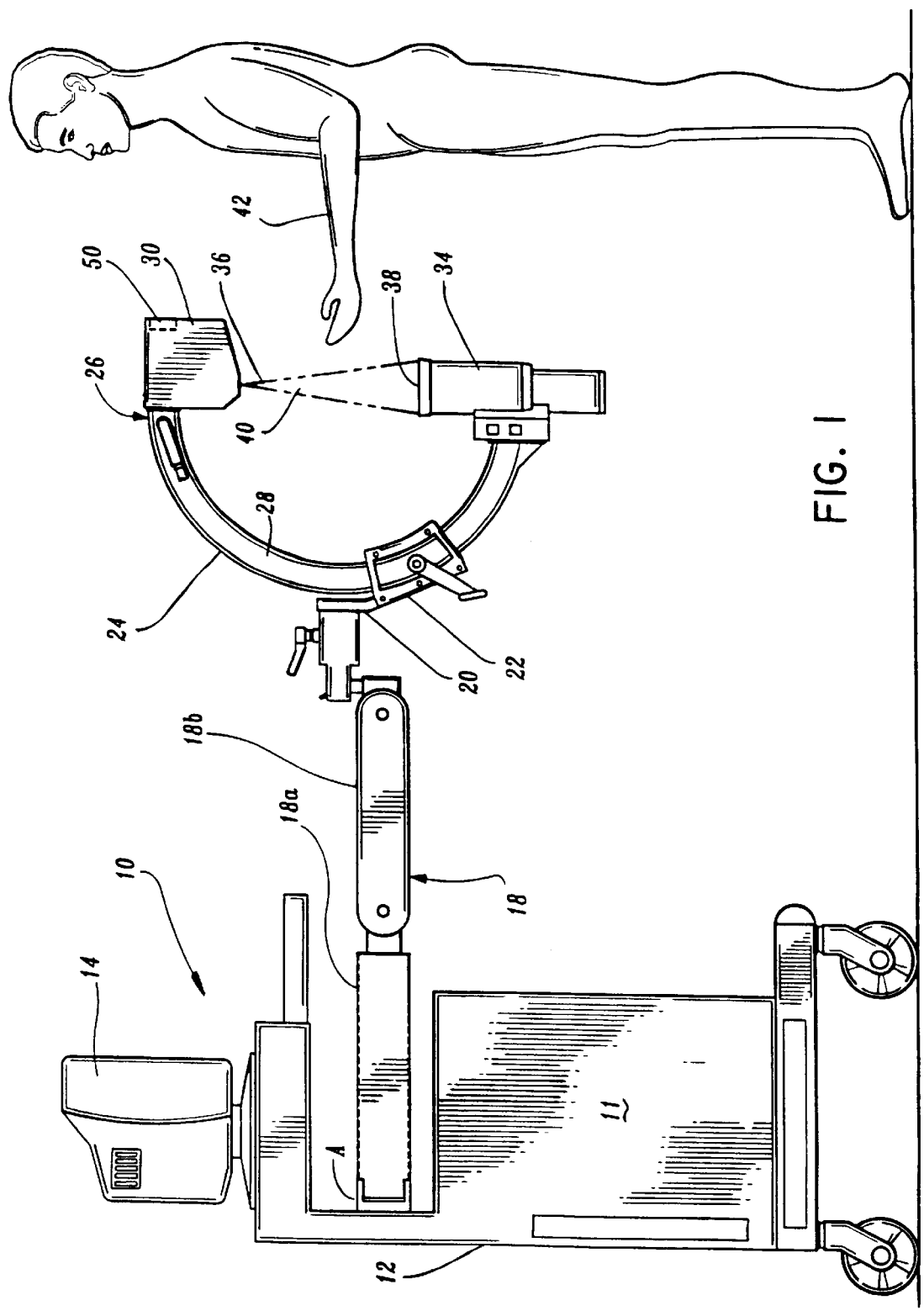
FIG. 1 is a simplified and partly schematic side elevational view of mini C-arm x-ray fluoroscopic imaging apparatus incorporating an illustrative embodiment of the present invention.
Figure 2:
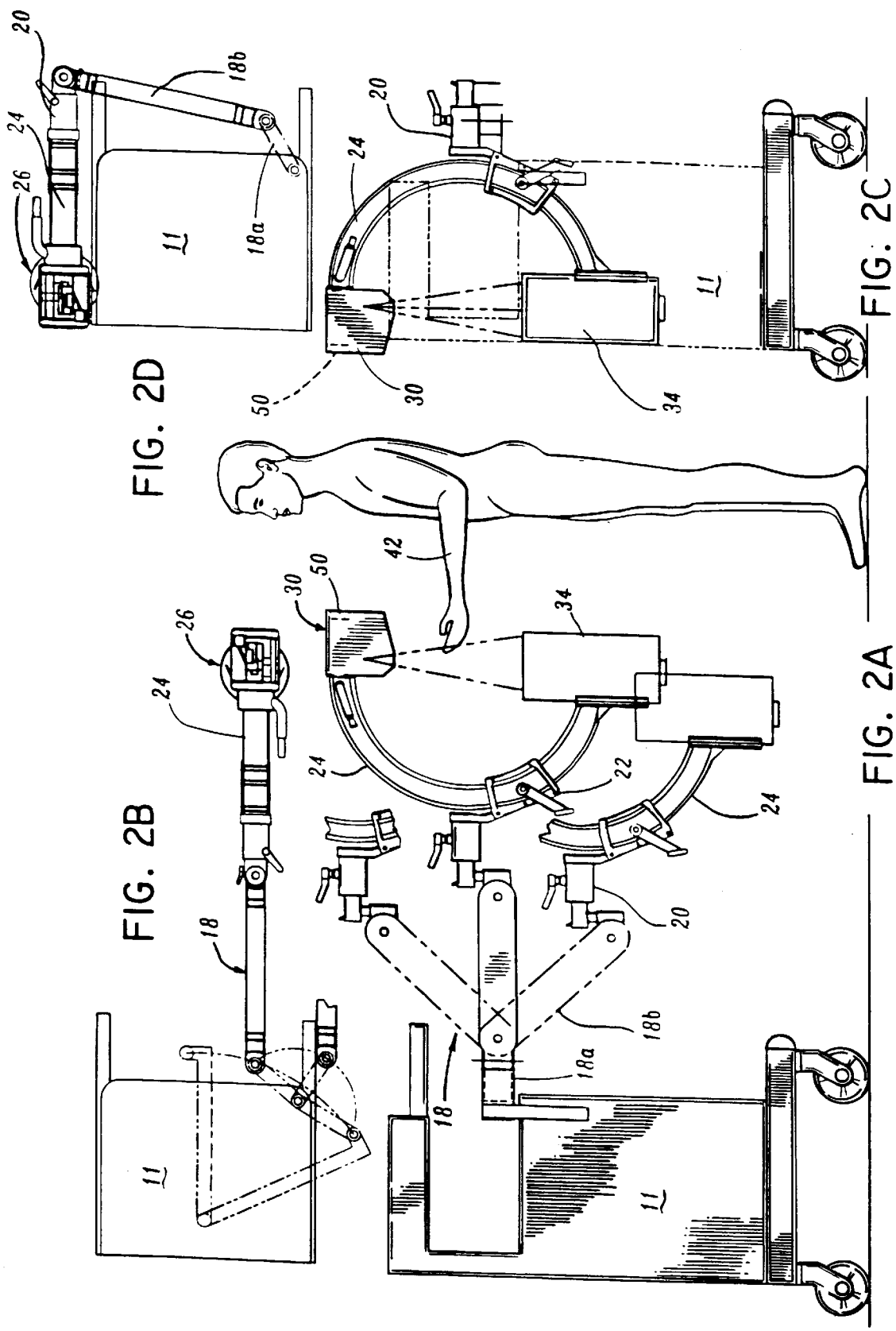
FIGS. 2A, 2B, 2C and 2D are reduced-scale views of the apparatus of FIG. 1, respectively in side elevation with the arm assembly extended (showing different positions thereof), in plan with the arm assembly extended, in side elevation with the arm assembly folded, and in plan with the arm assembly folded.
Figure 3:
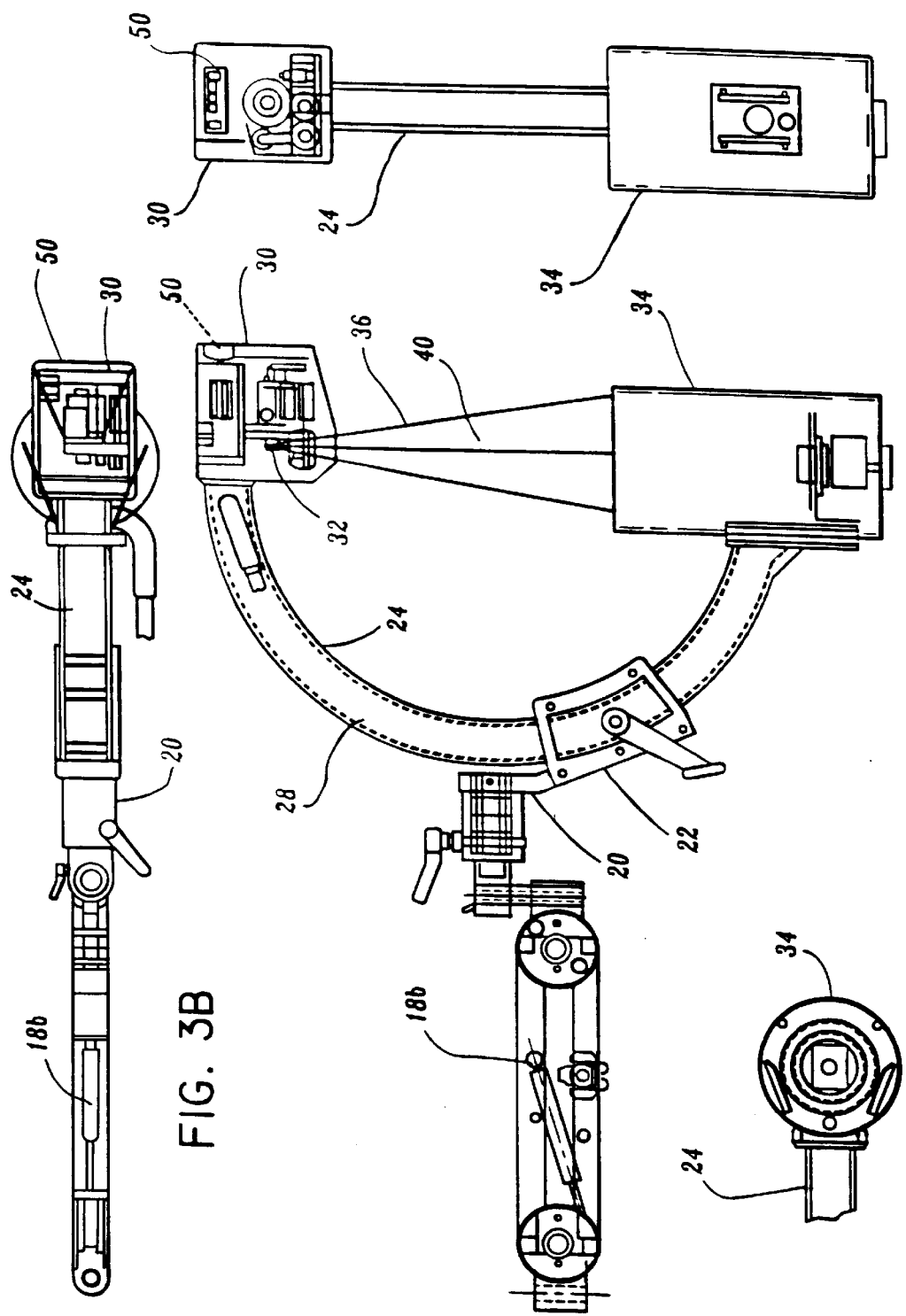
FIGS. 3A, 3B, 3C and 3D are enlarged views of a portion of FIG. 1, respectively in side elevation, top plan, fragmentary bottom plan, and front elevation.

An exemplary x-ray fluoroscopic imaging system incorporating one embodiment of the present application is shown in FIGS. 1–5. In this embodiment, the imaging system 10 is entirely contained in a wheeled cart or portable cabinet 11 that can easily be rolled from place to place. The cabinet includes a generally rectangular, upright body 12 that supports a display 14 (e.g., dual video monitors) on its top surface and an articulated arm assembly 18 secured thereto. The cabinet also contains a computer for processing data as hereinafter further discussed. It will be understood that images taken by the imaging system can be shown on only a single monitor, or printed on a printer which is preferably enclosed within the cabinet.

In this embodiment, the articulating arm assembly 18 includes two arms 18a and 18b. The distal end of arm 18b is connected to a support arm assembly 20 that has a C-arm locking mechanism 22. A C-arm 24 of mini C-arm assembly 26 is carried by the support arm assembly 20 such that a track 28 of the C-arm is slidable within the C-arm locking mechanism 22. The mini C-arm assembly 26 also includes an x-ray source assembly 30 and an x-ray detector assembly 34 respectively mounted at opposite extremities of the C-arm in facing relation to each other so that an x-ray beam 36 from an x-ray source 32 within the source assembly impinges on the input end 38 of the detector assembly 34. The x-ray source 32 and detector end 38 are spaced apart by the C-arm sufficiently to define a gap 40 between them, in which the limb or extremity of a human patient 42 can be inserted in the path of the x-ray beam 36.

The support arm assembly 20 connected to the end of arm 18b provides 3-way pivotal mounting that enables the C-arm 24 to be swivelled or rotated through 360° in each of three mutually perpendicular (x, y, z) planes and to be held stably at any desired position, while the arm 18a of the articulating arm assembly 18 is mounted to the portable cabinet 11 at point "A" and jointed to enable its distal end and the C-arm to be angularly displaced both horizontally and vertically. The multidirectional angular movability of the C-arm assembly facilitates the positioning of the x-ray source and detector assemblies in relation to a patient body portion to be irradiated.

A suitable power supply for the x-ray source, and instrumentalities for controlling or varying current (mA) and voltage (kV), not shown, are incorporated in the system as well.

As noted, the C-arm 24 is movable within the C-arm locking mechanism 22. To fix the position of the C-arm relative to the support arm assembly 20, the C-arm locking mechanism is used. The C-arm locking mechanism may be a clamp assembly (not shown) which is compressed against the C-arm when tightened, but preferably the C-arm locking mechanism is of the type described in pending U.S. Provisional Patent Applicaiton Ser. No. 60/066,966 filed on Nov. 28, 1997, which is incorporated herein in its entirety by this reference.

Figure 11:
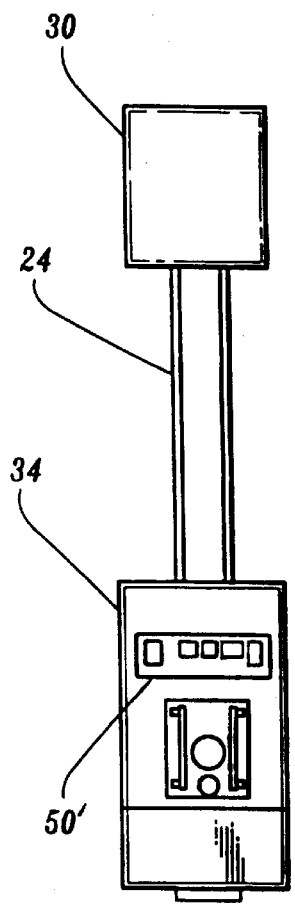
FIG. 11 is a view, similar to FIG. 3D, of a modified embodiment of the apparatus of the invention in which the C-arm control panel is mounted on the x-ray detector (receptor) assembly.
Figure 8:
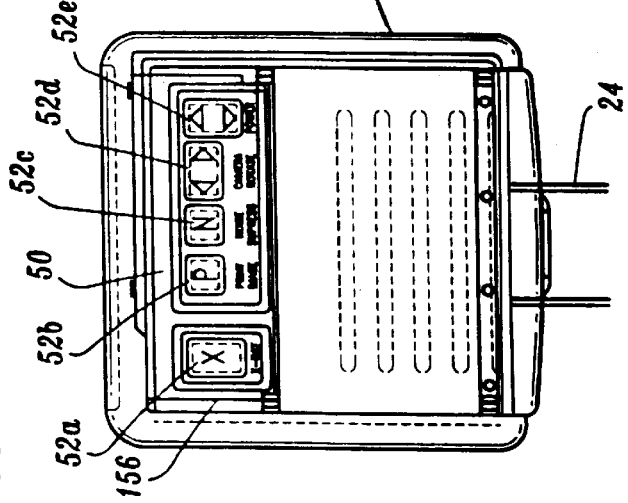

In accordance with the present invention, in its embodiments now to be described, either the x-ray source assembly or the x-ray detector assembly includes a control panel 50 or 50' that is mounted thereon (i.e. at one or the other of the opposed extremities of the C-arm) and is coupled to the imaging system computer to provide a physician with easy access within the sterile field to predefined imaging control functions associated with the x-ray fluoroscopic imaging system. In FIGS. 1–9, the control panel 50 is shown as mounted on the x-ray source assembly 22 at one end of the mini C-arm; in FIG. 11, the control panel 50' is illustrated as mounted on the x-ray detector assembly 34. With the control panel 50 or 50' included in either the source or detector assembly, a physician can activate certain (or all) functions of the x-ray fluoroscopic imaging system from within the sterile field and without placing a hand or arm within the path of the x-ray beam. One result of this configuration is that it gives a physician immediate control of the operating characteristics of the fluoroscope in the event that a regular operator is unavailable or unable to operate controls located outside of the sterile field. Preferably, as seen in FIG. 8, the control panel 50 includes an array of membrane switches 52a, 52b, 52c, 52d and 52e. Each switch in the array is provided to activate at least one function performed by the x-ray fluoroscopic imaging system. In one embodiment, each switch completes a signal circuit when contact material mounted on the underside of a raised button profile which provides tactile feedback is depressed to a base layer, and breaks the signal circuit when pressure on the contact material is released. As seen in FIG. 6D, each switch has a raised profile that is configured to provide a tactile response when depressed or released. This tactile response allows a physician wearing surgical gloves to feel when the switch is depressed or released.

Figure 6A:
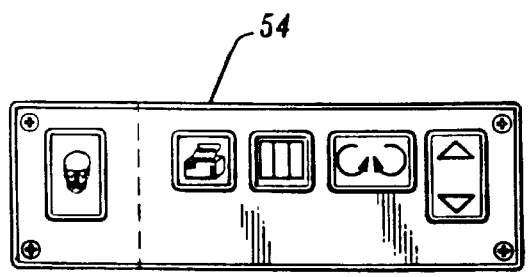
FIGS. 6A, 6B, 6C, 6D and 6E are, respectively, front elevational views of the button array, overlay, and assembled arrangement of the C-arm control panel of the apparatus of FIG. 1, and plan and side elevational views of the assembled arrangement of the control panel.
Figure 6B:
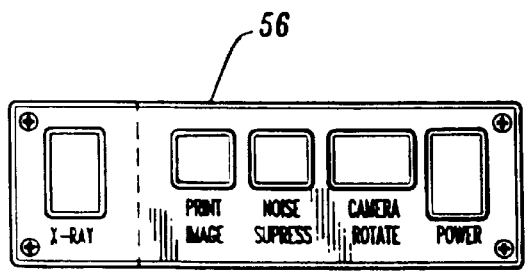
Figures 6C, 6E:
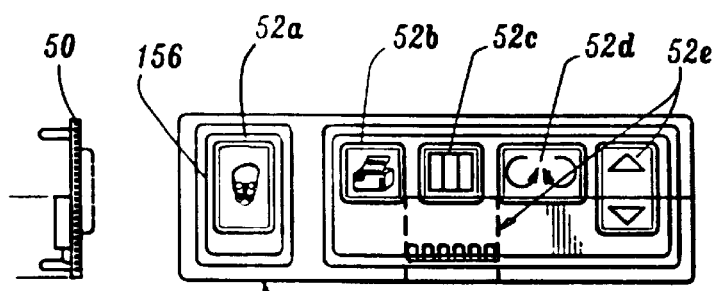
Figure 6D:
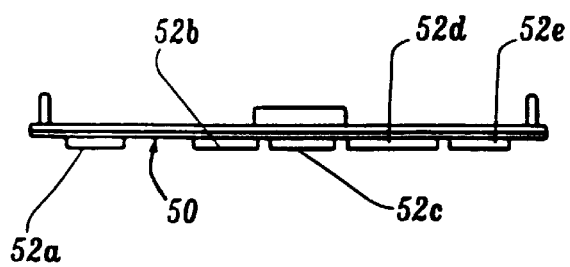
Figure 7:
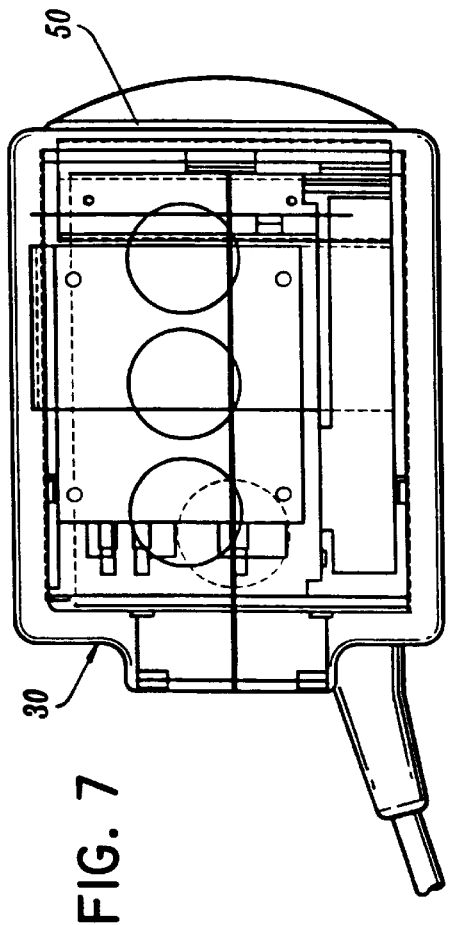
FIGS. 7, 8 and 9 are respectively top, front and side elevational views of the x-ray source assembly including the C-arm control panel in the apparatus of FIG. 1.
Figure 9:
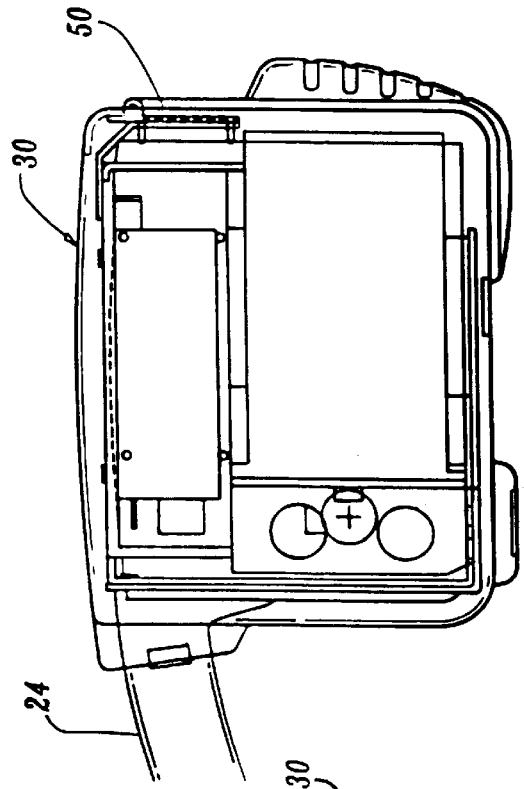

As further shown in FIGS. 6A and 6B, the control panel 50 includes a panel 54 bearing the array of membrane switches 52a–52e, and an overlay 56 with legends identifying the switches.

Examples of the functions activated by the control panel include:

X-ray Activation—One switch (designated 52a) in the array may control the x-ray source to generate a single image or for continuous imaging. For example, to generate a single image, a physician may depress the x-ray control switch twice in rapid succession and then release the switch so that the x-ray source (or tube) is activated for a single image or strobe shot. For continuous imaging, a physician depresses the x-ray control switch twice in rapid succession and then continues to depress (or hold down) the switch so that the x-ray source is activated and continues to produce x-rays for as long as the switch is depressed to create a real time continuous or cinematic fluoroscopic picture. Preferably this x-ray button or switch 52a is lighted red around its perimeter for ease of instant identification and avoidance of error, by the physician, as to which button or switch controls the x-ray source.

Print—One switch (designated 52b) in the array may control the imaging system's video printer by depressing the switch a single time. When the switch is depressed and released, the video printer is sent a signal from the system computer to print the active image.

Noise Suppression—One switch (designated 52c) in the array may control the imaging system's noise suppression processing by stepping the video frame averaging so that each time the switch is depressed the video noise suppression frame averaging is changed. For example, each depression of the switch can step the frame averaging from 0 frames to 2, 4, 8 and 16 frames successively, starting with a current frame averaging value and incrementing from there. When the frame averaging is at 16 and the switch is depressed the frame averaging value would then roll over to 0 and begin the rotation again.

Camera Rotation—One switch (designated 52d) in the array may control the imaging system's servo controlled camera mount. Activation of this switch activates a servo controller that rotates a camera mount in either a clockwise or counterclockwise direction. Feedback of the position of the camera mount within a range of travel of the servo controller may be provided by the use of a moving icon on the video display of the imaging system.

Voltage/Current Control—Typically the kV and mA settings of the imaging system are automatically set, but an up/down switch (designated 52e) in the array may allow a physician to manually control the fluoroscopic x-ray technique factors used to create an image by increasing or decreasing the kV and mA settings. Manual control can start with the current setting of the kV and mA values and can then be incrementally moved to the end points of the available settings with each depression of the up/down switch. The return to automatic control can be achieved by pressing both the up and down portions of the switch simultaneously.

Figure 10:
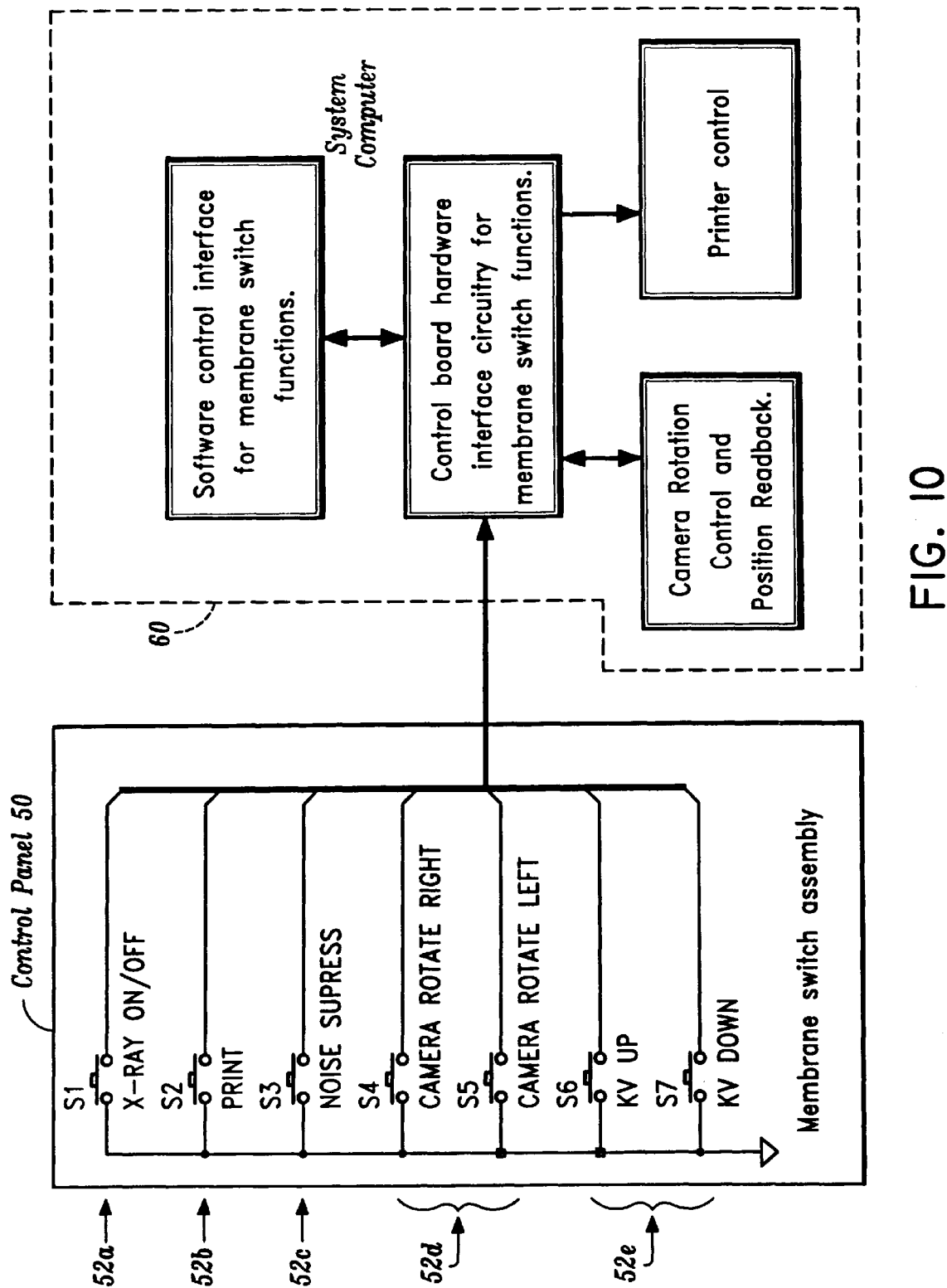
FIG. 10 is a block diagram of the control panel switches and their interaction with the system computer.

FIG. 10 provides a block diagram of the exemplary connections between the control panel switches and the system computer 60.

Figure 4:
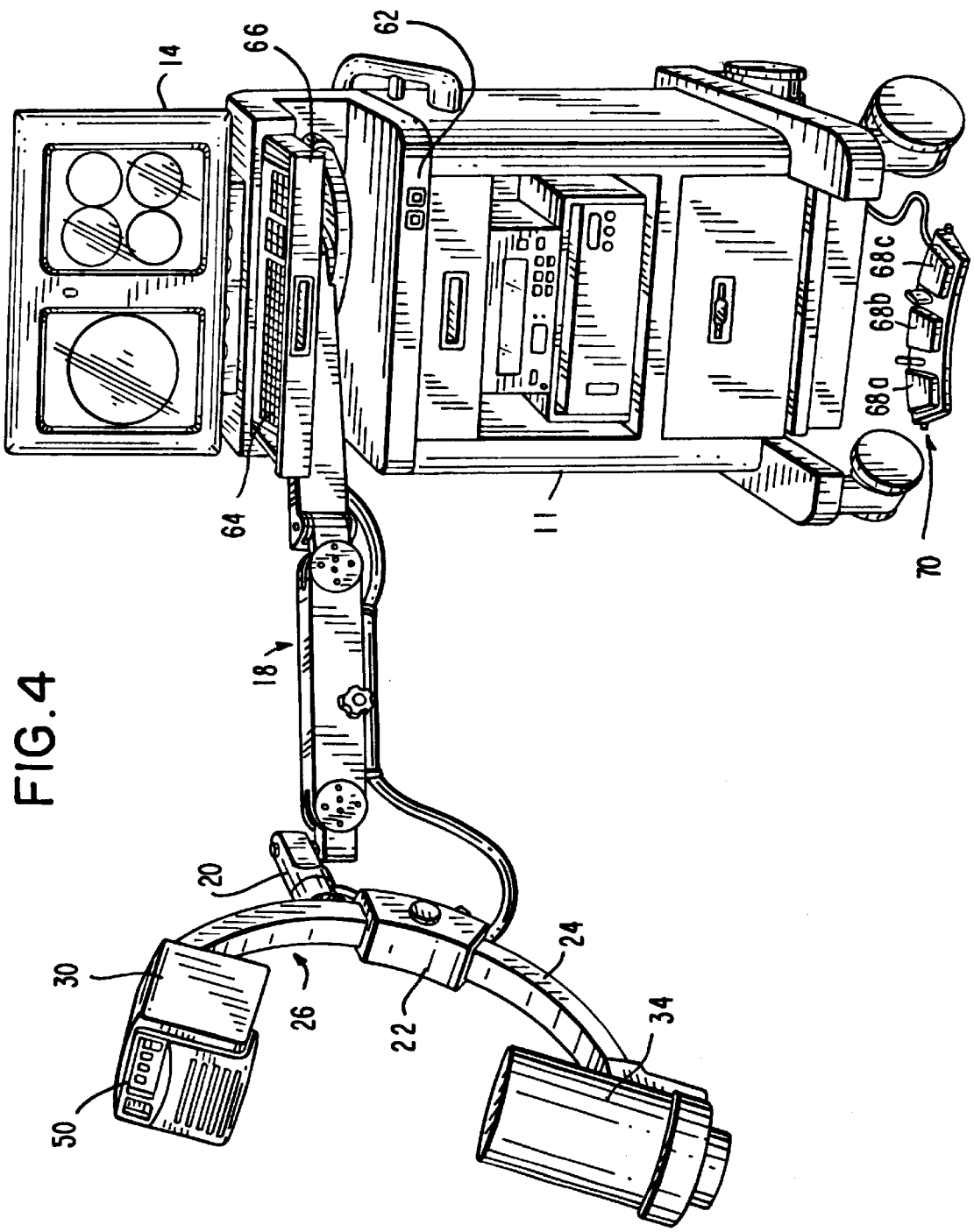
FIGS. 4 and 5 are perspective views of the apparatus of FIG. 1, respectively showing the C-arm in extended and folded positions.
Figure 5:
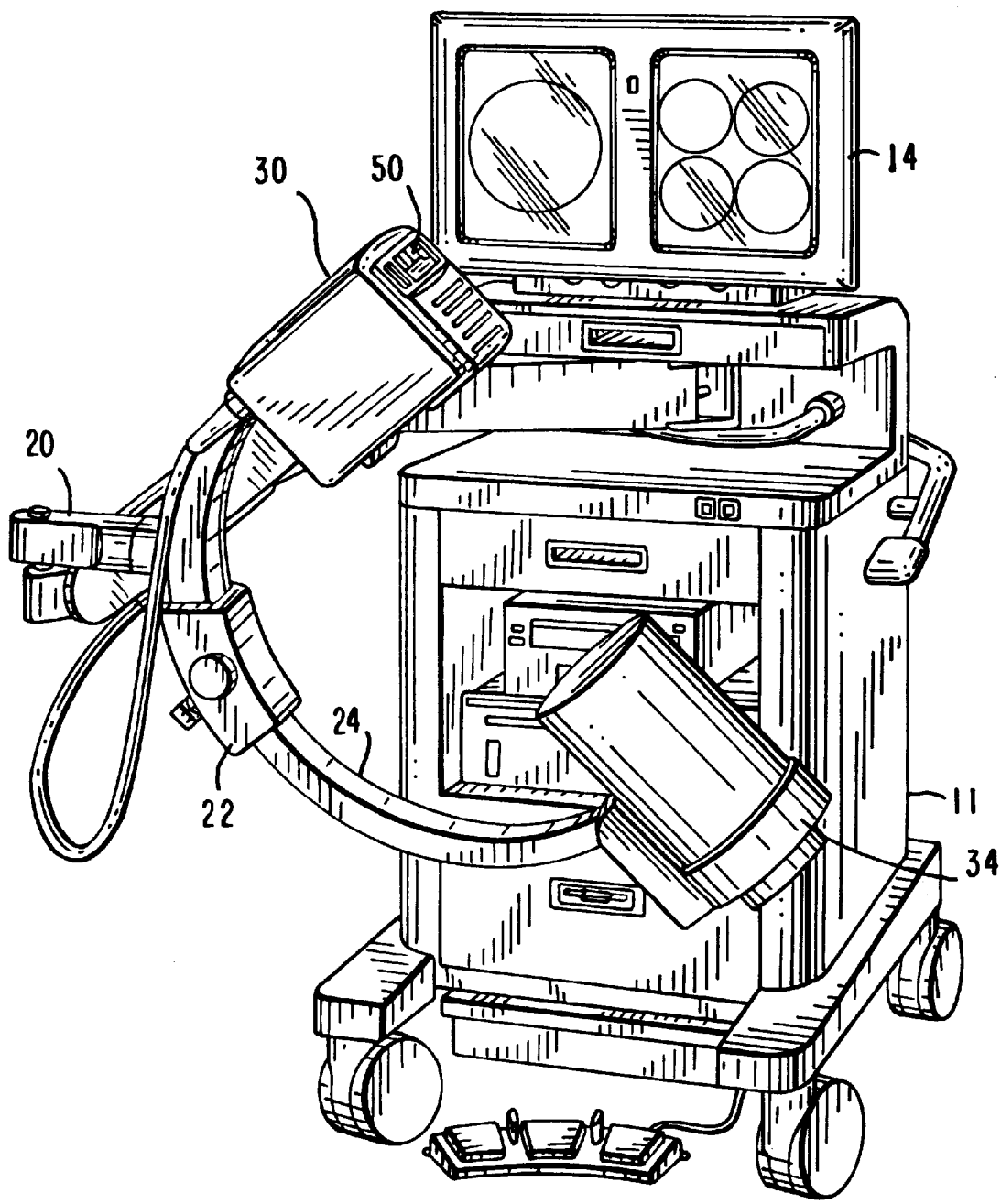

In addition to the switches or buttons of the control panel 50 or 50' mounted on the x-ray source or detector assembly, i.e. at one end or the other of the mini C-arm, so as to be positioned within the sterile field for direct access by the physician during use of the imaging system, the apparatus of FIGS. 1–5 also includes other controls, particularly shown in FIG. 4, such as switches 62 on the cabinet 11, a keyboard 64 for the computer 60, supported on a sliding shelf 66 of the cabinet, and an array of foot switches 68a, 68b and 68c on a foot control panel 70 which may, if desired, also be positioned within the sterile field for operation by the physician's foot. The switches on this foot control panel permit foot activation of predefined functions of the x-ray fluoroscopic imaging system including but not limited to x-ray activation, image printing and image storing.

An alternative embodiment of the x-ray fluoroscopic imaging system which can be used to measure bone mineral density (BMD) in, for example, the forearm, wrist, ankle or heel of a human patient will be described with reference to FIG. 12. This imaging system 100 is also entirely contained in a wheeled cart or cabinet 110 that can easily be rolled from place to place. The cabinet includes a generally rectangular, upright body 112 that supports dual video monitors 114 (only one being shown) on its top surface and has, in its upper portion, a keyboard 116 and an articulated member 118; the cabinet also contains a computer (not shown) for processing data as hereinafter further discussed. It will be understood that the present method can be practiced with use of only a single monitor, or indeed without a monitor (e.g., employing a printer to produce the BMD measurement data).

The outer end of articulated member 118 carries a mini C-arm 120 having an x-ray source 122 and a detector 124 respectively fixedly mounted at its opposite extremities so that an x-ray beam 126 from source 122 impinges on the input end 128 of the detector, the source and detector being spaced apart by the C-arm sufficiently to define a gap 129 between them, in which the limb or extremity of a human patient 130 can be inserted in the path of the x-ray beam 126. The C-arm is connected to the end of member 118 by a 3-way pivotal mounting 132 that enables the C-arm to be swivelled or rotated through 360° in each of three mutually perpendicular (x, y, z) planes and to be held stably at any desired position, while the member 118 is itself mounted and jointed to enable its outer end and the C-arm to be angularly displaced both horizontally and vertically. The multidirectional angular movability of the mini C-arm facilitates the positioning of the source and detector in relation to a patient body portion to be irradiated.

Preferably, either the x-ray source or the x-ray detector includes a control panel 150 that is coupled to the imaging system computer to provide a physician with easy access within the sterile field to predefined imaging control functions associated with the x-ray fluoroscopic imaging system. The control panel 150 is illustrated in FIG. 12 as being mounted on the detector 124. Preferably, the control panel 150, like the panel 50 of FIG. 8, includes an array of membrane switches, each of which is provided to activate at least one function performed by the x-ray fluoroscopic imaging system. In one embodiment, each switch in the array has a raised button profile which provides tactile feedback, completes a signal circuit when contact material mounted on the underside of the raised button profile which provides tactile feedback is depressed to a base layer and breaks the signal circuit when pressure on the contact material is released.

A suitable power supply for the x-ray source, and instrumentalities for controlling or varying current (mA) and voltage (kV), not shown, are incorporated in the system as well.

The beam 126 emitted by the x-ray source 122 is a cone-shaped beam (i.e. a volume beam as opposed to a pencil beam or fan beam) that impinges on a flat x-ray-sensitive receiving surface of the detector 124 at or adjacent the detector input end; this receiving surface faces the source across the gap 129 and is perpendicular to the axis of the beam path, so that the intersection of the receiving surface and the conical x-ray beam is an extended circular (2-dimensional) area. The term "field of view" is used herein to refer to the latter circular area, or that portion of it to which the detector responds, and also to designate the region, within the beam path or gap 129, the contents of which will be imaged by the detector. It will be understood that the area of the field of view as measured in a plane transverse to the beam path axis is sufficient to encompass objects of the size desired to be imaged or otherwise studied, e.g. a human wrist or heel.

The receiving surface of the detector 124 is a surface of an x-ray-to-visible-light converter, such as a layer of phosphor or scintillator material covered externally by a light shield, that converts impinging x-rays to visible light. The detector may include a Cesium Iodide vacuum tube image intensifier or an image intensifier of the high-gain micro-channel plate type, and a planar output surface on which is produced an output visible-light image of the field of view, in accordance with well-known principles of fluoroscopic imaging. The combined converter and image intensifier elements of the detector 124 may be as described in the aforementioned U.S. Pat. No. 4,142,101 which is incorporated herein by reference.

In addition, the detector assembly includes a video camera (not separately shown) for viewing the image on the aforementioned planar output surface and producing a signal output representative of that viewed image. The video camera can be a television camera and can operate according to a video standard such as NTSC or CCIR. When the system is employed for fluoroscopic imaging, the signal output of the video camera is processed by the onboard computer to produce video images on one or both monitors 114; the system also includes devices for recording and, optionally, printing out these video fluoroscopic images.

As thus far described, the system 100 is essentially identical to currently available mini C-arm x-ray fluoroscopic imaging systems. Thus, the system 100 may be a "FluoroScan III" system, having the following pertinent specifications:

OUTPUT FORMAT

Standard 2,200 Image Storage;

Optional 4,000 Image Storage; Digital Video Output;

Composite Video Output

VIDEO PROCESSING

Last Image Hold for 4 Images;

Real Time Edge Enhancement;

User Selectable Real Time Recursive Averaging;

Noise Suppression; Automatic Contrast Enhancement;

Automatic Brightness Control

INPUT POWER

110V~60 Hz Nominal; 90V~ to 132V~Actual; 47 Hz to 63 Hz Actual; Non Dedicated, Grounded

WARM UP

3 Seconds

X-RAY POWER SUPPLY

Continuous Duty kV–40 kV to 75 kV in 2.15 kV Increments

ANODE CURRENT

20 $\mu$A to (0.020 mA) to 100 $\mu$A (0.1 mA) in 3.6 $\mu$A Increments

FOCAL SPOT

85 Micron (0.085 mm)

TUBE TYPE

Custom Designed Cold Anode

TUBE COOLING

Maximum Tube Temperature is 50° C. at Maximum Power After 4 Hours of Continuous Duty

TARGET

Tungsten

COLLIMATION

Fixed to Field of View Size

FIELDS OF VIEW 75 mm (3" Nominal)

100 mm (4" Nominal)

125 mm (5" Nominal)

IMAGE INTENSIFIER

High Gain Micro Channel Plate with Minimum of 40,000 Gain

PIXEL ARRAY 768 pixels by 600 lines

DUAL VIDEO MONITORS

14" (36 cm) SVGA High Resolution Video Monitor

Video Standard NTSC/VHS

OVERALL HEIGHT 53 inches

OVERALL FLOOR SPACE 4.7 ft$^2$ (25" wide by 27" deep)

Since the detector in the fluoroscopic imaging system detects x-ray emission from a cone-beam source over an extended two-dimensional area (the cross-section of the x-ray beam path in the plane of the detector receiving surface), there is inherent variation (i.e., variation attributable to the source and/or the detector having the image intensifier, independent of attenuation by any object interposed in the beam path) in received radiation intensity over the field of view. The image data obtained for the wrist and calibration bone sample by the steps described above are corrected for this inherent variation in order to enable more accurate calculation of BMD.

A wide variety of additional alternatives are embraced within the scope of the invention in its broader aspects. For instance, the image intensifier employed in the detector may be either of a type that intensifies optical images (as in the above-described "FluoroScan III" system) or of a type that intensifies x-ray images. Again, in place of an image intensifier and video camera, the detector may be a direct digital 2-dimensional x-ray detector; an example of such a device is the "FlashScan 20" high resolution flat panel device of dpiX, A Xerox Company, which is an amorphous silicon image sensor that acquires conventional x-ray images and converts them to digital form in a way that can provide fluoroscopic imaging in real time.

The calculation of data to produce BMD measurements could be performed with an onboard computer in a mini C-arm fluoroscopic system such as the "FluoroScan III" system, or in another computer. The functions of data acquisition/storage and BMD computation therefrom could be performed by different computers. Also, instead of digitizing the detector output data before conversion to logarithms, the logarithmic conversion could be performed first (e.g. with a log amplifier) and digitized thereafter. Moreover, in addition to or in place of the fixtures described above for holding the body portion stationary, appropriate software could be employed to re-register the images if there is movement.

A more detailed description of this embodiment and its operation is provided in the aforementioned U.S. application Ser. No. 08/794,615 which is incorporated herein by reference.

It is to be understood that the invention is not limited to the procedures and embodiments hereinabove specifically set forth, but may be carried out in other ways without departure from its spirit.

What is claimed is:

1. An x-ray fluoroscopic imaging system comprising:
    a portable cabinet;
    an articulating arm assembly having at least one movable arm wherein a first end portion of said at least one movable arm is connected to said portable cabinet and a second end portion of said at least one movable arm is connected to a support arm assembly; and
    a C-arm assembly having a C-arm carried by said support arm assembly, an x-ray source assembly including an x-ray source and an x-ray detector assembly including an image receptor located at opposing locations on the C-arm such that said x-ray source and image receptor face each other so that x-rays emitted by said x-ray source impinge on said image receptor, wherein at least one of said source and image receptor assemblies includes a control panel coupled to a computer in said x-ray fluoroscopic imaging system that permits activation of predefined functions of the x-ray fluoroscopic imaging system.

2. The imaging system according to claim 1 further comprising
    a foot control panel that permits activation of predefined functions of the x-ray fluoroscopic imaging system.

3. The imaging system according to claim 1, wherein said control panel comprises a plurality of switches, and wherein each switch permits activation of a predefined function of the x-ray fluoroscopic imaging system.

4. The imaging system according to claim 1, wherein said control panel comprises an array of membrane switches, each switch completing a signal circuit when depressed and breaking said signal circuit when released.

5. The imaging system according to claim 1, wherein said control panel comprises an array of membrane switches, and wherein each switch has a raised button profile, completes a signal circuit when the contact material mounted on the underside of said raised button profile is depressed to a base layer, and breaks said signal circuit when pressure on said contact material is released.

6. The imaging systems according to claim 2, wherein said foot control panel comprises a plurality of switches, and wherein each switch permits activation of a predefined function of the x-ray fluoroscopic imaging system.

7. The imaging systems according to claim 2, wherein said foot control panel comprises an array of membrane switches, each switch completing a signal circuit when depressed and breaking said signal circuit when released.

8. The imaging system according to claim 1, wherein said control panel comprises an array of membrane switches, and wherein each switch has a raised button profile, completes a signal circuit when the contact material mounted on the underside of said raised button profile is depressed to a base layer, and breaks said signal circuit when pressure on said contact material is released.

* * * * *